United States Patent
LoPresto (10) Patent No.: US 10,093,426 B2
(45) Date of Patent: Oct. 9, 2018

(54) SUPER-COOLED WATER-DROPLET SIZE INDICATOR

(71) Applicant: Rosemount Aerospace Inc., Burnsville, MN (US)

(72) Inventor: Vincent R. LoPresto, Eagan, MN (US)

(73) Assignee: Rosemount Aerospace Inc., Burnsville, MN (US)

( * ) Notice: Subject to any disclaimer, the term of this patent is extended or adjusted under 35 U.S.C. 154(b) by 102 days.

(21) Appl. No.: 15/332,843

(22) Filed: Oct. 24, 2016

(65) Prior Publication Data

US 2018/0111694 A1 Apr. 26, 2018

(51) Int. Cl.
*B64D 15/20* (2006.01)
*G01B 5/14* (2006.01)
*G01N 15/00* (2006.01)

(52) U.S. Cl.
CPC ............. *B64D 15/20* (2013.01); *G01N 15/00* (2013.01)

(58) Field of Classification Search
CPC ........ B64D 15/20; B64D 45/00; B64D 47/08; G08B 19/02; G01N 15/0227; G01P 13/025

USPC ............... 702/127, 155, 128; 244/17.11, 134
See application file for complete search history.

(56) References Cited

U.S. PATENT DOCUMENTS

| | | | |
|---|---|---|---|
| 3,604,660 A | 9/1971 | Marley | |
| 6,269,320 B1 | 7/2001 | Otto | |
| 8,944,383 B2 | 2/2015 | Bellussi et al. | |
| 2017/0369176 A1* | 12/2017 | LoPresto | B64D 15/20 |
| 2017/0369177 A1* | 12/2017 | LoPresto | B64D 15/20 |

* cited by examiner

*Primary Examiner* — John H Le
(74) *Attorney, Agent, or Firm* — Kinney & Lange, P.A.

(57) ABSTRACT

Apparatus and associated devices relate to a system for measuring a maximum size of super-cooled water droplets in a cloud atmosphere. The system includes a housing having a convex exterior surface on a forward end and having stabilizers projecting from an aft end. The system includes a gimballed mounting mechanism configured to attach the housing to an aircraft while permitting the housing to freely pitch and yaw with respect to the aircraft. When an airstream engages the stabilizers, the housing aligns with a direction of the engaging airstream. The system includes a sequence of indices on a corresponding sequence of ice-accretion regions of the convex exterior surface, each of the sequence of indices visible in the absence of ice accretion. The forward-most ice-free one of the sequence of indices is indicative of a maximum size of super-cooled water droplets.

19 Claims, 8 Drawing Sheets

SUPER-COOLED WATER-DROPLET SIZE INDICATOR

BACKGROUND

Certain atmospheric conditions can lead to ice formation on aircraft surfaces. Ice formation on aircraft surfaces can increase the weight of the aircraft and can increase the drag of the aircraft. Increasing either the weight or the drag of an aircraft can result in a stall speed that is higher than it would otherwise be in an ice-free condition. Ice formation on lifting surfaces can result in a decrease in a wing's lift and/or a decrease in a propeller's thrust. Ice formation can also affect the controllability of an aircraft by affecting the airflow over control surfaces, such as ailerons.

Various atmospheric conditions can cause more or less ice formation on an aircraft. For example, water droplet density, total moisture content, air temperature, water droplet temperature, droplet size distribution, etc. all factor into risk of ice formation. Some atmospheric conditions can present little or no risk of ice formation on an aircraft.

Various aircraft flying conditions can affect locations and/or amounts of ice formation on aircraft surfaces. For example, airspeed, angle of attack, angle of side-slip, and presence of de-icing equipment all factor into location and/or risk of ice formation.

Some aircraft have been equipped with equipment intended to obtain various metrics of the atmosphere so as to predict whether the atmosphere presents a risk of ice-formation on exterior surfaces. Ice formation on aircraft surfaces can be visually perceived by the pilot, should the ice form on a surface within view of the cockpit window.

SUMMARY

Apparatus and associated devices relate to a super-cooled water-droplet size measurement system. The super-cooled water-droplet size measurement system includes a housing having a convex exterior surface on a forward end and having stabilizers projecting from an aft end. The super-cooled water-droplet size measurement system includes a gimballed mounting mechanism configured to attach the housing to an aircraft while permitting the housing to freely pitch and yaw with respect to the aircraft. When an airstream engages the stabilizers, the housing aligns with a direction of the engaging airstream. The super-cooled water-droplet size measurement system includes a sequence of indices on a corresponding sequence of ice-accretion regions of the convex exterior forward-facing surface, each of the sequence of indices visible in the absence of ice accretion. The sequence of ice-accretion regions accretes ice when the engaging airstream contains super-cooled water droplets of at least a corresponding sequence of predetermined minimum sizes.

Some embodiments relate to a method for indicating of a maximum size of super-cooled water droplets in an airstream. The method includes engaging an airstream of an aircraft by a housing having a convex exterior surface on a forward end and having fins projecting from an aft surface. The method includes aligning, using the fins, the housing in a direction of the engaged airstream. The method includes providing a sequence of visual indices corresponding to a sequence of ice-accretion regions, each of the sequence of indices visible in the absence of ice accretion. The method also includes accreting ice on one or more of the sequence of ice-accretion regions when the engaged airstream contains super-cooled water droplets.

DETAILED DESCRIPTION

Apparatus and associated methods relate to determining, based on a spatial extent of ice accretion, whether an atmosphere contains super-cooled water droplets that equal and/or exceed a predetermined size. A housing is mounted to an aircraft and exposed to an airstream. The housing has a convex-shaped exterior surface on a forward end and stabilizers projecting from an aft end. The convex-shaped housing is mounted on a gimballed mechanism that facilitates the convex-shaped housing to align itself with an engaging airstream. The convex-shaped exterior surface has a testing region that has indicia for monitoring an extent of ice accretion. As ice accretes from a leading edge of the convex-shaped housing one or more of the indicia can become obscured by the ice-accretion, starting with a leading one of the indicia. The closest index from the leading index in an ice-free region is indicative of a maximum size of super-cooled water droplets in the airstream.

Figure 1:
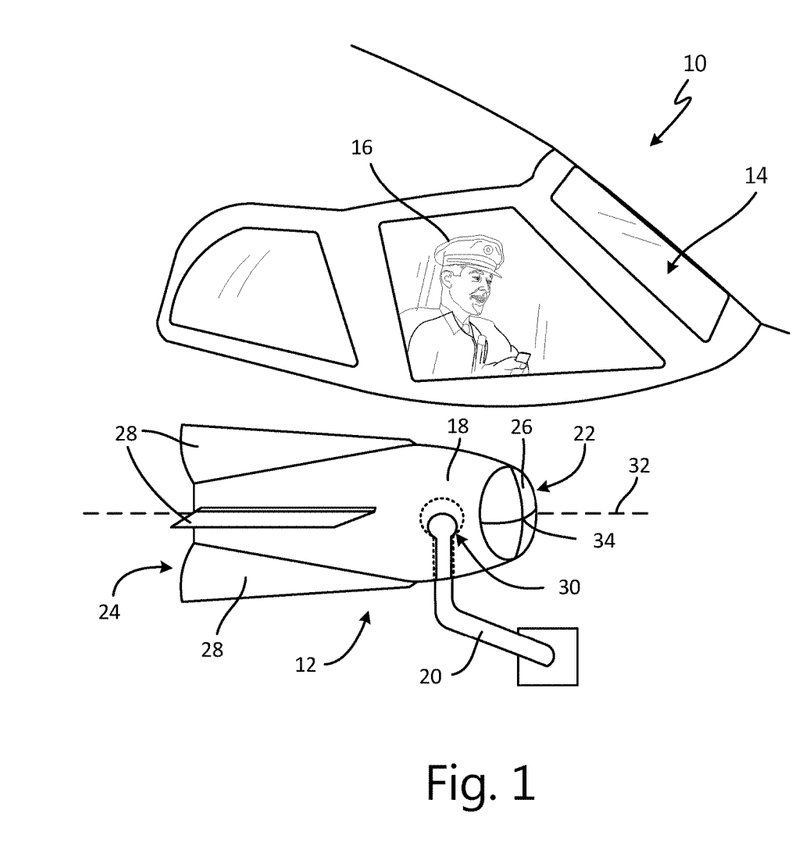
FIG. 1 is a perspective view of an exemplary weather-vane styled ice detector.

FIG. 1 is a perspective view of an exemplary weather-vane styled ice detector. In FIG. 1, aircraft 10 is equipped with an exemplary weather-vane styled or self-aligning (e.g., with an airstream) ice detector 12. Ice detector 12 is mounted outside of cockpit 14 so as to be visible by pilot 16. Ice detector 12 includes housing 18 and gimballed attachment mechanism 20. Housing 18 includes forward end 22 and aft end 24. Forward end 22 has convex exterior surface 26, and aft end 24 has fins 28. Ice detector 12 is attached to aircraft 10 via gimballed attachment mechanism 20. Gimballed attachment mechanism 20 is configured to provide at least two degrees of freedom of movement of ice detector 12 with respect to aircraft 10. In some embodiments, gimballed attachment mechanism 20 facilitates pitch and yaw rotations of ice detector 12. For example, gimballed attachment mechanism may have ball-and-socket mechanism 30. Fins 28 can engage an airstream, and when so engaged, the airstream may orient housing 18 so as to align housing 18 with a direction of the airstream. When housing 18 is aligned with the direction of the airstream, axis 32 will be parallel with the direction of the airstream and axial center point 34 will be the leading point of housing 18 in the airstream. When housing 18 is so aligned with an airstream having super-cooled water droplets, ice will accrete about axial center point 34 in a substantially symmetric fashion.

In atmospheric conditions having super-cooled water droplets, ice can accrete on convex exterior surface 26 from axial center point 34 and aft therefrom. Locations where ice accretion occurs on convex exterior surface 26 can indicate a maximum size of super-cooled water droplets in the atmosphere. Specifically a location of a border that separates regions of ice accretion from ice-free regions can be indicative of the maximum size of super-cooled water droplets. Ice may accrete from axial center point 34 to a distance aft of axial center point 34. The distance aft of axial center point 34 where ice accretion ceases can correspond to the maximum size of super-cooled water droplets in the atmosphere. Providing a visual indicator of this distance of ice accretion can facilitate a pilot's knowledge of atmospheric conditions.

Figure 2:
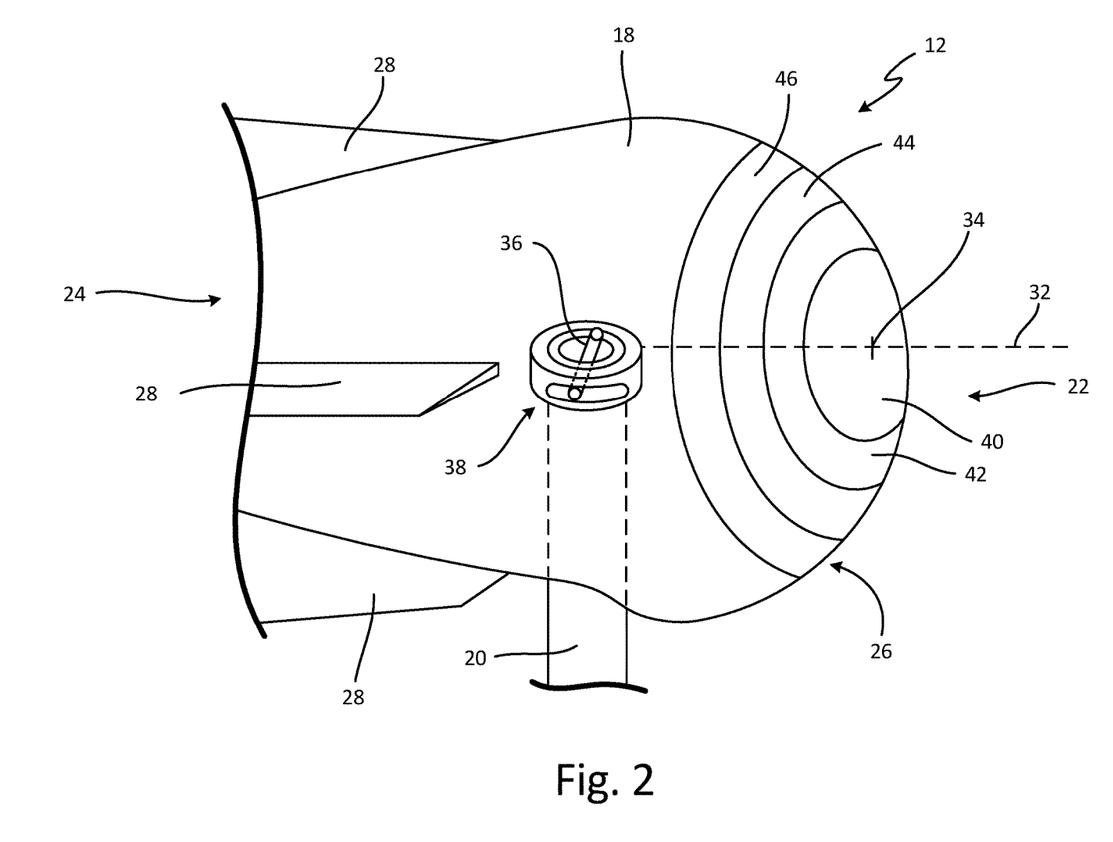
FIG. 2 is a perspective view of a gimballed mounted ice detector showing exemplary visual indices.

FIG. 2 is a perspective view of a gimballed mounted ice detector showing exemplary visual indices. In FIG. 2, ice detector 12 includes housing 18 and gimballed attachment mechanism 20. Housing 18 has forward end 22 and aft end 24. Forward end 22 has convex exterior surface 26, and aft end 24 has fins 28 projecting therefrom. Gimballed attachment mechanism 20 provides for pitch and yaw rotation with respect to an airplane to which it is attached. In the depicted embodiment, gimballed attachment mechanism 20 has pivoting mechanism 36 to facilitate free pitch movement, and has rotating collar 38 to facilitate free yaw movement. Various embodiments may use various mechanisms to provide freedom of movement of housing 18 with respect to an aircraft to which it is attached via gimballed attachment mechanism 20.

In the depicted embodiment, visual indices 40, 42, 44 and 46 are arranged about axial center point 34 in a bullseye fashion. Each of the sequence of visual indices 40, 42, 44 and 46 is circularly symmetric about axis 32, and axial center point 34, as is convex exterior surface 26. Each of the sequence of visual indices 40, 42, 44 and 46 corresponds to a region of convex exterior surface 26 upon which ice accretion will occur, in conditions conducive to ice-accretion, when super-cooled water droplets exceeding a predetermined minimum size are present. For example, in the region corresponding to visual index 40, ice accretion can occur when super-cooled water particles are present within the atmosphere of any size, including very small super-cooled water particles. In the region corresponding to visual index 42, however, ice-accretion can occur only when super-cooled water particles larger than some first predetermined minimum size are present in the atmosphere. In the region corresponding to visual index 44, ice-accretion can occur only when super-cooled water particles larger than some second predetermined minimum size greater than the first predetermined minimum size are present in the atmosphere. In the region corresponding to visual index 46, ice-accretion can occur only when super-cooled water particles larger than some third predetermined minimum size greater than the second predetermined minimum size are present in the atmosphere.

Various embodiments can have various configurations of visual indices as well as various geometries of convex exterior surface 26. In some embodiments, visual indices 40, 42, 44 and 46 will be determined using complex fluid dynamic analyses of the specific housing 18 in various atmospheric conditions. When ice accretes upon one or more of visual indices 40, 42, 44 and 46, the visual indicator can either be obscured or can be otherwise visually changed so that a pilot and/or an optical detector can detect the presence of ice thereon.

Figure 3:
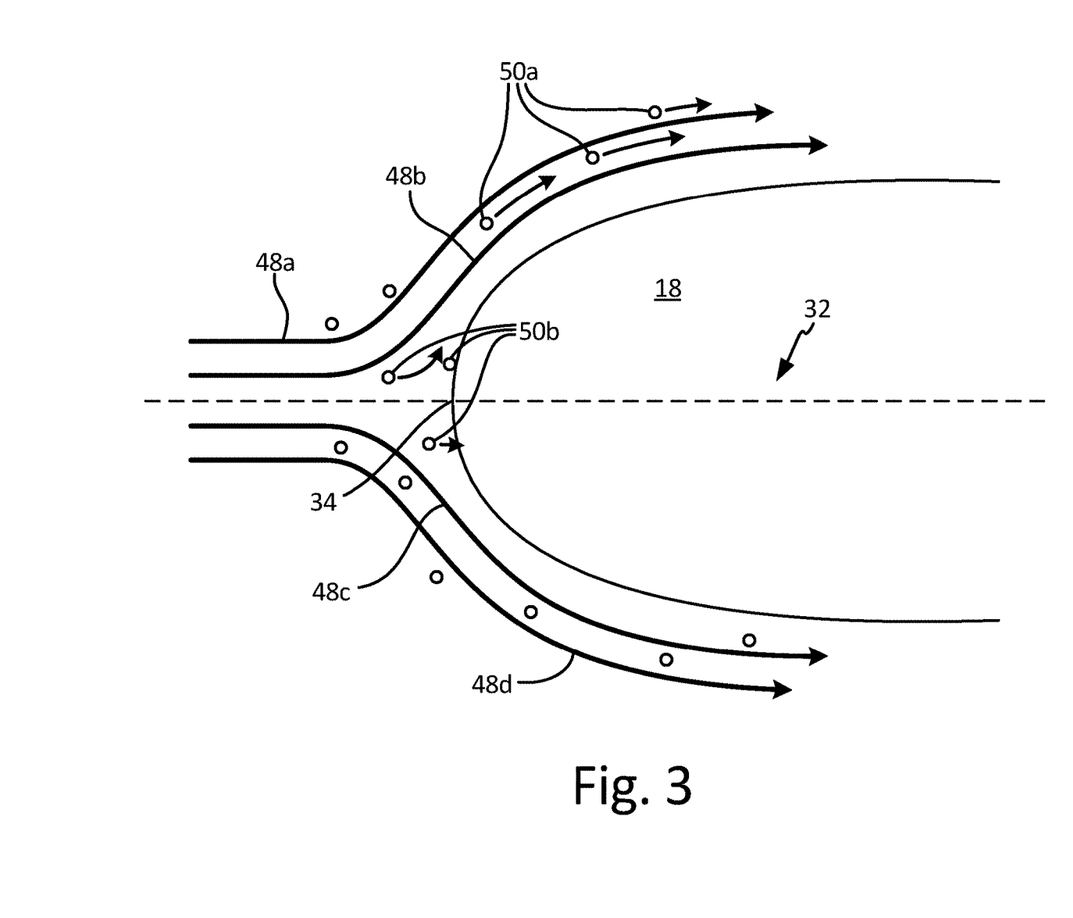
FIG. 3 is a schematic diagram of ice accreting on a leading edge of a curved member in an airstream.

FIG. 3 is a schematic diagram of ice accreting on a leading edge of a curved member in an airstream. In FIG. 3, three-dimensional housing 18 is shown in cross section. Housing 18 has flow-dividing axis 32 aligned with a general direction of airflow. Airflow is represented by flow vectors 48a, 48b, 48c and 48d. Water droplets 50a and 50b are carried by the airflow. Small water droplets 50a generally follow the flow vectors, because the mass of the small water droplets 50a is small. A momentum of the small water droplets 50a is correspondingly small, because of the small mass. Because the momentum is small for small water droplets, changing the direction, and thus the momentum, of these small water droplets can be achieved by small forces, such as those imparted by flow vectors 48a, 48b, 48c and 48d. Small water droplets 50a impinge housing 18 only proximate flow-dividing axis 32 at leading edge 34.

Large water droplets 50b, however, have momentums that are larger than those of small water droplets 50a, due to larger masses of the large water droplets 50b. Such large water droplets 50b do not follow flow vectors 48a, 48b, 48c and 48d as readily as do small water droplets 50a. Because large water droplets 50b more readily cross flow vectors 48a, 48b, 48c and 48d, such large water droplets 50b impinge housing 18 along a greater section of leading edge 34 than is impinged by small water droplets 50a. Large water droplets 50b impinge housing 18 proximate flow-dividing axis 32 at leading edge 34 as do small water droplets 50a. Large water droplets 50b also impinge housing 18 aft of leading edge 34 for a distance that is related to the droplet size. Airflow does impart a force on large water droplets 50b, and therefore large water droplets 50b do experience momentum change. Because large water droplets 50b can undergo such momentum change, these large water droplets impinge housing 18 only over a limited range about leading edge 34.

If water droplets 50a and 50b are super-cooled (e.g., at temperatures below a freezing temperature of water), then such particles can freeze upon impact with housing 18 or another object (e.g., a fuselage, etc.). Pure water can be super-cooled without freezing in the absence of a nucleation site. Such a scenario is not infrequent in cloud atmospheres. The shock of impingement and/or the structural nucleation sites presented by the impinging object can cause such super-cooled water droplets to freeze almost immediately upon such an impingement event.

Figure 4:
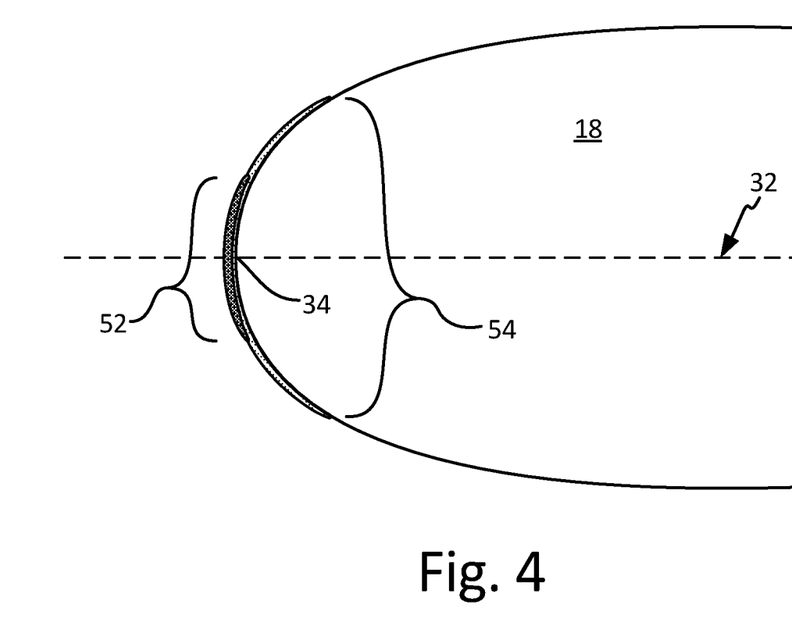
FIG. 4 is a schematic diagram depicting different zones of ice-accretion associated with different sizes of super-cooled water droplets.

FIG. 4 is a schematic diagram depicting different zones of ice-accretion associated with different sizes of super-cooled water droplets. In FIG. 4, housing 18 depicted in FIG. 3 is shown in magnification to demonstrate a relationship between water droplet size and impingement region. Two different impingement regions 52, 54 are depicted proximate leading edge 34 of housing 18. Impingement region 52 corresponds to a small region about leading edge 34.

Small impingement region 52 is a region in which water droplets, which are less than or equal to a relatively small size (such as small water droplets 50a depicted in FIG. 2), can impinge, for a given set of aircraft and flying conditions. Small water droplets 50a can readily follow flow vectors 48a, 48b, 48c and 48d (depicted in FIG. 3). Flow vectors 48a and 48b show an airflow pattern above housing 18, and flow vectors 48c and 48d show an airflow pattern below housing 18. Flow vectors 48a and 48b diverge from flow vectors 48c and 48d about central axis 32. Only at locations along leading edge 34 that are proximate central axis 32 can small water droplets 50a impinge housing 18. The intersection of leading edge 34 and flow-dividing axis 32 can be called the stagnation point.

Large impingement region 54 includes portions of housing 18 which can be impinged only by water droplets that are larger than a predetermined size (such as large water droplets 50b depicted in FIG. 3) for a given set of aircraft and flying conditions. Because larger water droplets 50b can cross flow vectors 48a, 48b, 48c and 48d more readily than can small water droplets 50a, such large water droplets 50b impinge housing 18 within larger region (e.g., large impingement region 54) about leading edge 34 than the region (e.g., small impingement region 52) impinged by small water droplets 50a. In this way, FIG. 4 demonstrates a relation that exists between a size of water droplets and a regional area in which such sized water droplets are capable of impingement.

Figure 5:
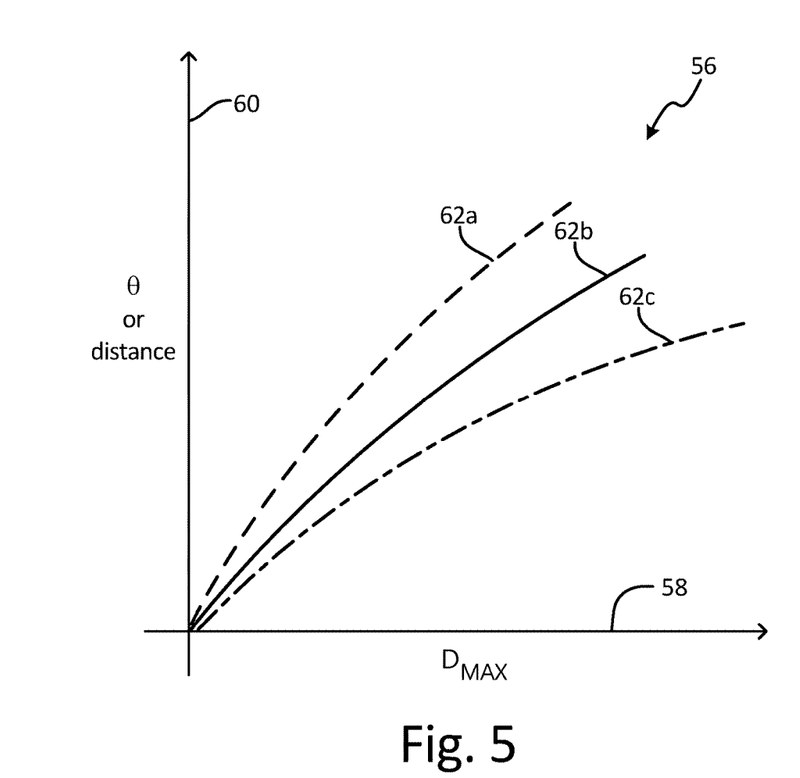
FIG. 5 is a graph of exemplary relations of size of an ice-accretion region versus size of super-cooled water droplets.

FIG. 5 is a graph of exemplary relations of size of an ice-accretion region versus size of super-cooled water droplets. In FIG. 5, graph 56 has horizontal axis 58 and vertical axis 60. Horizontal axis 58 represents maximum size $D_{MAX}$ of water droplets in an atmosphere. Vertical axis 60 represents a distance dimension (e.g., angle θ from the stagnation point or chord length d from the stagnation point) of impingement region. Graph 56 has three relations 62a, 62b and 62c. Relation 62a represents a relation between maximum size $D_{MAX}$ of water droplets and the distance dimension of impingement region for a first set of icing conditions. Relations 62b and 62c represent relations between maximum size $D_{MAX}$ of water droplets and the distance dimension of impingement region for a second and a third set of icing conditions, respectively.

Parameters that affect icing conditions can include aircraft conditions, flying conditions, and atmospheric conditions, for example. Aircraft conditions can include, for example, a shape of a structure on which water droplets impinge, temperature of a surface of the impingement region, aircraft configuration, etc. Flying conditions can include, for example, an angle of attack, an angle of side-slip, an airspeed, water droplet temperature, liquid water content, etc. Atmospheric conditions can include air temperature, air pressure, etc. Various embodiments may be more or less affected by one or more of the icing conditions. For example, some embodiments may be more or less sensitive to angle of attack. A structure that presents substantially the same shape to the airflow independent of angle of attack, for example, may be not very sensitive to angle of attack. Some geometries may be less sensitive to angle of sideslip, for example.

Figure 6:
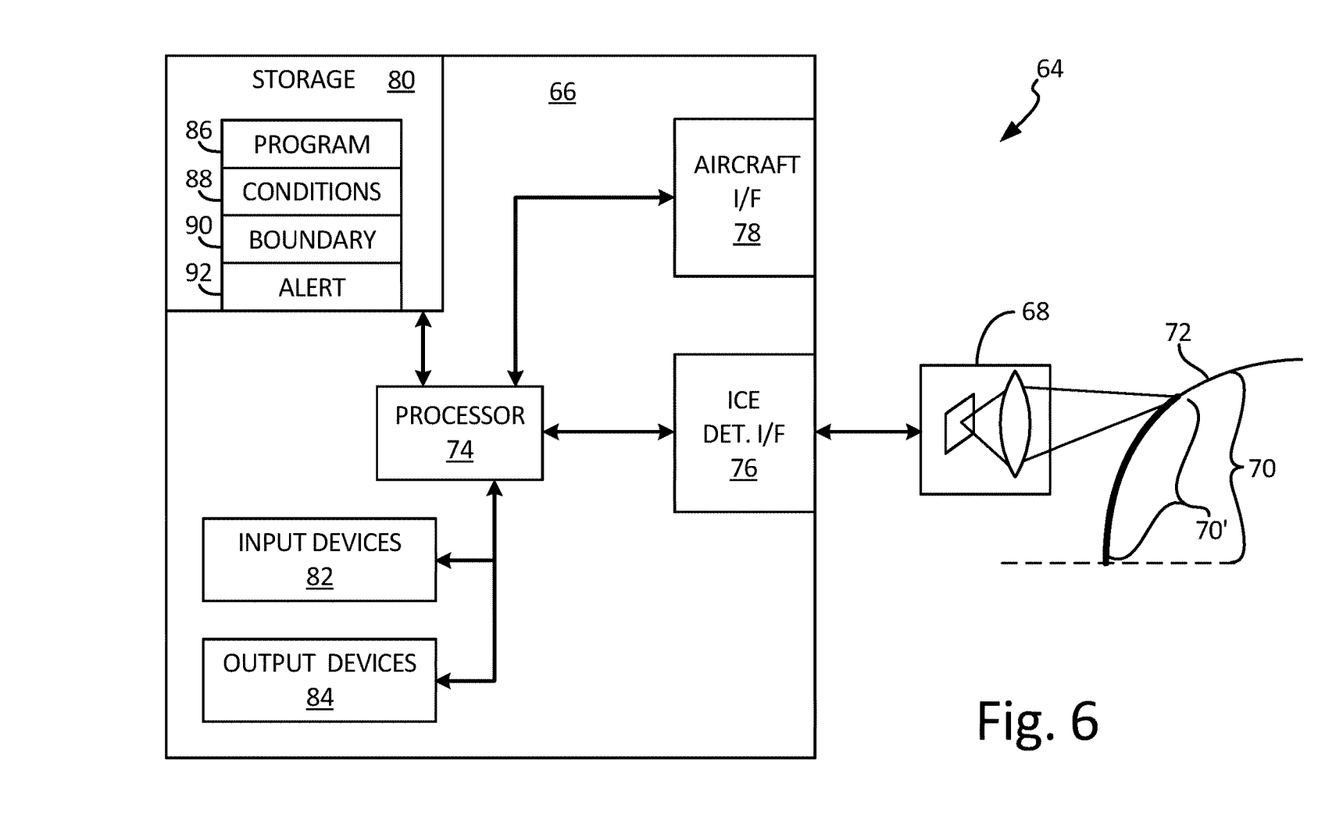
FIG. 6 is a block diagram of an exemplary ice-accretion alert system.

FIG. 6 is a block diagram of an exemplary ice-accretion alert system. In FIG. 6, ice-accretion alert system 64 includes controller 66, ice detector 68 and testing region 70 of convex exterior surface 26 of housing 18 (depicted in FIGS. 1-2). Controller 66 includes processor(s) 74, ice detector interface 76, aircraft interface 78, storage device(s) 80, user input devices 82, and user output devices 84. Storage device(s) 80 has various storage or memory locations. Storage device(s) 80 includes program memory 86, conditions data memory 88, boundary calculation module 90, and alert module 92. Controller 66 is in communication with ice detector 68. Ice detector 68 is configured to monitor ice accretion on testing region 70. Testing region 70 is depicted with ice-accretion portion 70' upon which ice has accreted.

As illustrated in FIG. 6, controller 66 includes processor(s) 74, ice detector interface 76, aircraft interface 78, storage device(s) 80, user input devices 82, and user output devices 84. However, in certain examples, controller 66 can include more or fewer components. For instance, in examples where controller 66 is an avionics unit, controller 66 may not include user input devices 82 and/or user output devices 84. In some examples, such as where controller 66 is a mobile or portable device such as a laptop computer, controller 66 may include additional components such as a battery that provides power to components of controller 66 during operation.

Processor(s) 74, in one example, is configured to implement functionality and/or process instructions for execution within controller 66. For instance, processor(s) 74 can be capable of processing instructions stored in storage device(s) 80. Examples of processor(s) 74 can include any one or more of a microprocessor, a controller, a digital signal processor (DSP), an application specific integrated circuit (ASIC), a field-programmable gate array (FPGA), or other equivalent discrete or integrated logic circuitry.

Storage device(s) 80 can be configured to store information within controller 66 during operation. Storage device(s) 80, in some examples, is described as computer-readable storage media. In some examples, a computer-readable storage medium can include a non-transitory medium. The term "non-transitory" can indicate that the storage medium is not embodied in a carrier wave or a propagated signal. In certain examples, a non-transitory storage medium can store data that can, over time, change (e.g., in RAM or cache). In some examples, storage device(s) 80 is a temporary memory, meaning that a primary purpose of storage device(s) 80 is not long-term storage. Storage device(s) 80, in some examples, is described as volatile memory, meaning that storage device(s) 80 do not maintain stored contents when power to controller 66 is turned off. Examples of volatile memories can include random access memories (RAM), dynamic random access memories (DRAM), static random access memories (SRAM), and other forms of volatile memories. In some examples, storage device(s) 80 is used to store program instructions for execution by processor(s) 74. Storage device(s) 80, in one example, is used by software or applications running on controller 66 (e.g., a software program implementing long-range cloud conditions detection) to temporarily store information during program execution.

Storage device(s) 80, in some examples, also include one or more computer-readable storage media. Storage device(s) 80 can be configured to store larger amounts of information than volatile memory. Storage device(s) 80 can further be configured for long-term storage of information. In some examples, storage device(s) 80 include non-volatile storage elements. Examples of such non-volatile storage elements can include magnetic hard discs, optical discs, flash memories, or forms of electrically programmable memories (EPROM) or electrically erasable and programmable (EEPROM) memories.

Ice detector interface 76, in some examples, includes a communications module. Ice detector interface 76, in one example, utilizes the communications module to communicate with external devices via one or more networks, such as one or more wireless or wired networks or both. The communications module can be a network interface card, such as an Ethernet card, an optical transceiver, a radio frequency transceiver, or any other type of device that can send and receive information. Other examples of such network interfaces can include Bluetooth, 3G, 4G, and Wi-Fi 33 radio computing devices as well as Universal Serial Bus (USB).

Aircraft interface 78 can be used to communicate information between controller 66 and an aircraft. In some embodiments, such information can include aircraft conditions, flying conditions, and/or atmospheric conditions. In some embodiments, such information can include data processed by controller 66, such as, for example, alert signals.

Aircraft interface 78 can also include a communications module. Aircraft interface 78, in one example, utilizes the communications module to communicate with external devices via one or more networks, such as one or more wireless or wired networks or both. The communications module can be a network interface card, such as an Ethernet card, an optical transceiver, a radio frequency transceiver, or any other type of device that can send and receive information. Other examples of such network interfaces can include Bluetooth, 3G, 4G, and Wi-Fi radio computing devices as well as Universal Serial Bus (USB). In some embodiments, communication with the aircraft can be performed via a communications bus, such as, for example, an Aeronautical Radio, Incorporated (ARINC) standard communications protocol. In an exemplary embodiment, aircraft communication with the aircraft can be performed via a communications bus, such as, for example, a Controller Area Network (CAN) bus.

User input devices 82, in some examples, are configured to receive input from a user. Examples of user input devices 82 can include a mouse, a keyboard, a microphone, a camera device, a presence-sensitive and/or touch-sensitive display, push buttons, arrow keys, or other type of device configured to receive input from a user. In some embodiments, input communication from the user can be performed via a communications bus, such as, for example, an Aeronautical Radio, Incorporated (ARINC) standard communications protocol. In an exemplary embodiment, user input communication from the user can be performed via a communications bus, such as, for example, a Controller Area Network (CAN) bus.

User output devices 84 can be configured to provide output to a user. Examples of user output devices 84 can include a display device, a sound card, a video graphics card, a speaker, a cathode ray tube (CRT) monitor, a liquid crystal display (LCD), a light emitting diode (LED) display, an organic light emitting diode (OLED) display, or other type of device for outputting information in a form understandable to users or machines. In some embodiments, output communication to the user can be performed via a communications bus, such as, for example, an Aeronautical Radio, Incorporated (ARINC) standard communications protocol. In an exemplary embodiment, output communication to the user can be performed via a communications bus, such as, for example, a Controller Area Network (CAN) bus.

Figure 7:
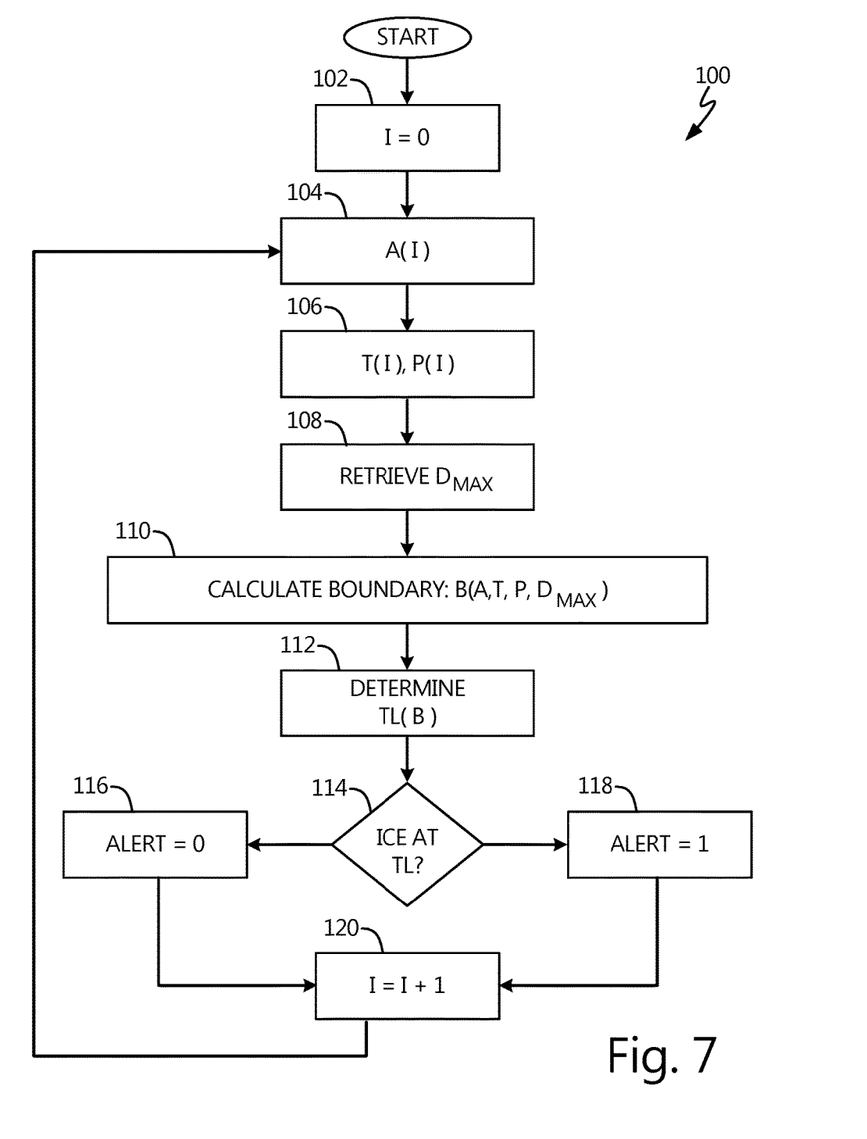
FIG. 7 is a flow chart of an exemplary method for generating an alert if atmosphere exterior to an aircraft has super-cooled water droplets exceeding a predetermined size.

FIG. 7 is a flow chart of an exemplary method for generating an alert if atmosphere exterior to an aircraft has super-cooled water droplets exceeding a predetermined size. In FIG. 7, method 100 is depicted from the vantage point of processor(s) 74 of FIG. 6. Method 100 begins at step 102 where processor(s) 74 initializes index I. Then, at step 104, processor(s) 74 receives, from the aircraft, aircraft conditions including airspeed A(I). The method then proceeds to step 106 where processor(s) 74 receives, from the aircraft, atmospheric conditions including temperature T(I) and pressure P(I). The method proceeds to step 108 where processor(s) 74 retrieves, from data memory, a maximum water droplet size $D_{MAX}$.

The method then proceeds to step 110 where processor(s) 74 calculates a boundary location B(I) based on the received aircraft conditions, A(I), the received atmospheric conditions, T(I) and P(I), and the retrieved maximum water droplet size $D_{MAX}$. Then at step 112, processor(s) 74 determines a location TL(I) within a testing region that corresponds to the calculated boundary location B(I). Method 100 proceeds to step 114 where processor(s) 74 receives, from the ice detector 68 (depicted in FIG. 6) a signal indicative of ice formation at the determined location TL(I). Processor(s) 74 evaluates whether ice has formed at the determined location TL(I) based on the received signal. If, at step 114, processor(s) 74 determine that ice has not formed at the determined location TL(I), then at step 116 processor(s) 74 clears the alert signal ALERT. If, however, at step 114, processor(s) 74 determines that ice has formed at the determined location TL(I), then at step 118 processor(s) 74 sets the alert signal ALERT. Method 100 proceeds from steps 116 and/or 118 to step 120, at which processor(s) 74 increments index I. Then, method 100 returns to step 104 and repeats.

In some embodiments, the output of an ice-accretion detection system can determine a maximum super-cooled water-droplet size based on a measured extent of ice formation indicated on a convex-exterior surface of the housing. The ice-accretion detection system can provide, as an output, a signal indicative of the determined maximum super-cooled water-droplet size. This output signal may then be used by a receiving system to determine whether an alert signal is generated.

In an exemplary embodiment, a super-cooled water-droplet size distribution of an atmosphere exterior to an aircraft can be calculated. Distinct locations on an exterior surface of an aircraft may be susceptible to ice accretion arising from super-cooled water droplets exceeding a predetermined size striking the distinct location. For example, ice may form at each distinct location, only if the atmosphere external to the aircraft includes super-cooled water droplets that exceed the predetermined size corresponding to that distinct location. By measuring a rate of ice accretion at a plurality of locations along a chord from the stagnation point toward an aft location, a water-droplet size distribution can be calculated.

For example, ice may accrete at a boundary location that separates an ice-accretion region from an ice-free region due to an atmosphere that has super-cooled water-droplets up to a maximum size. Only the super-cooled water droplets that are of the maximum size may cause ice-accretion at the boundary location. And then, at locations more forward from the boundary location, ice may accrete due to super-cooled water-droplets that have sizes that span between a lower threshold and the maximum size. As one travels toward the stagnation point, ice accretes due to a span of sizes of super-cooled water droplets that includes smaller and smaller sizes. By measuring the amount and/or the rate of ice accretion at each of these points, a reconstruction of a super-cooled water-droplet size distribution can be calculated In some embodiments, a heating system is repeatedly used to melt, evaporate, and/or sublimate ice accreted on the testing region. Such a heating system can facilitate testing in conditions in which ice accretion slows or stops due to improving atmospheric conditions. After melting or sublimating any accreted ice from the testing region, the heater may be turned off so that ice may again accrete if conditions permit such accretion. In an exemplary embodiment, the heater can be operated cyclically, such that each cycle has a heating portion, an ice accretion portion, and an ice detection portion. The heater can be activated during the heating portion and deactivated during the ice accretion and ice detection portions. Such an embodiment may repeatedly evaluate ice accretion so as to provide current icing data to a user.

Various flying conditions can cause variations in local cooling of exterior surfaces of the aircraft and of the housing. For example, local variations in airspeed proximate surfaces of the aircraft can cause local cooling variations. Ice formation conditions can therefore vary locally as well. For example, the icing conditions of the housing may not be exactly the same as the icing conditions of a surface location of an aircraft. In some embodiments, a temperature control system can control a temperature of the housing, so as to better align icing conditions of the housing with those of various surface locations of the aircraft to which the housing is attached. In some embodiment, the temperature control system can be used simply to ensure that the exterior surface of the housing is cool enough to cause icing so that a maximum droplet size can be determined. For example, a cooling system can be configured to actively cool the convex exterior surface of the housing.

Such temperature control systems can also be used to heat the testing regions so as to sublimate, melt, and/or evaporate ice accreted to such regions. Such temperature control capabilities can be used to provide cycles of operation that include a heating portion, an accretion portion, and a sensing portion. The heater can be activated during the heating portion to remove any ice accreted to the testing region. The heater can then be deactivated during the accretion portion and during the sensing portions. In some embodiments, the testing region can be cooled, before or during the accretion and/or sensing portions. The ice detector can then be activated during the sensing portion. Some embodiments can include an alert system to generate an alert if the ice detector detects ice at testing locations indicative of super-cooled water droplets having sizes that exceed a predetermined threshold.

Figure 8:
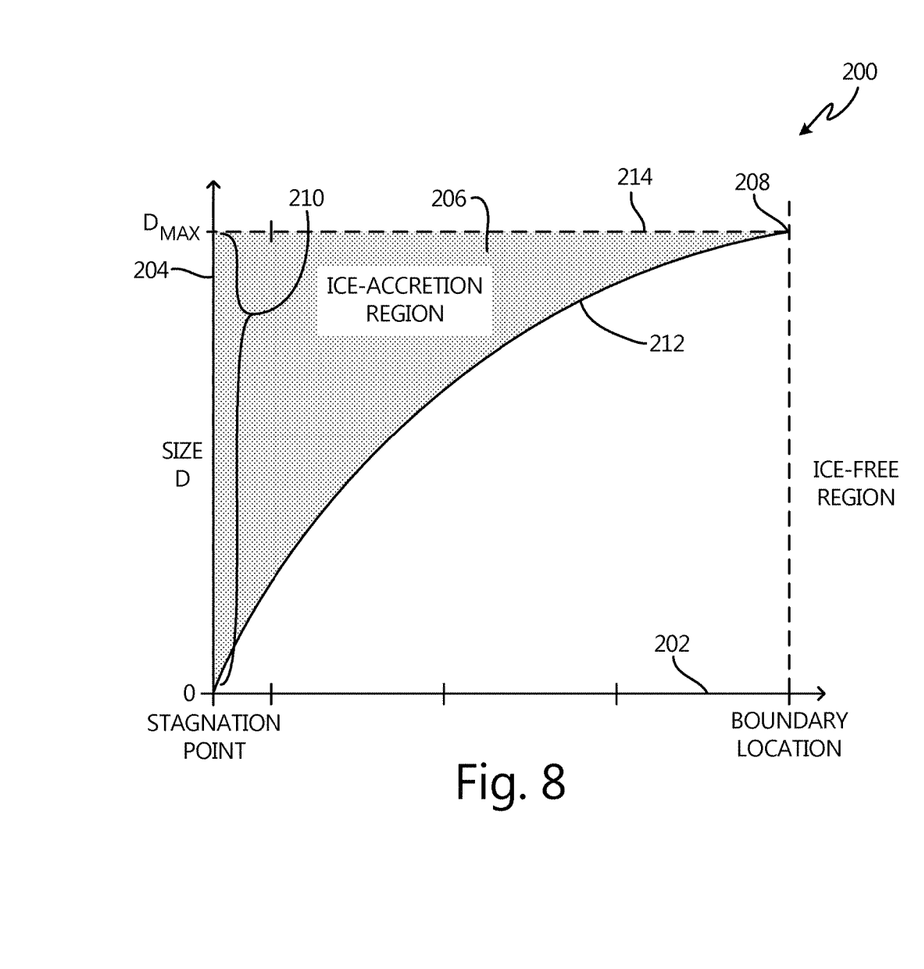
FIG. 8 is a graph depicting a size span of water-droplets vs. location along a chord of a convex-shaped housing.

FIG. 8 is a graph depicting a size span of water-droplets vs. location along a chord of a convex-shaped housing. In FIG. 8, graph 200 has horizontal axis 202 and vertical axis 204. Horizontal axis 202 represents location along a chord of a convex exterior surface exposed to an atmosphere containing super-cooled water droplets. Vertical axis 204 represents a size of the super-cooled water droplets. Graph 200 includes droplet size/location relation 206 corresponding to a size of super-cooled droplets that can strike the convex exterior surface at the indicated location. For example, at a given location along the convex-shaped housing (e.g., draw a vertical line from any x-axis location), the exterior surface of the convex-shaped housing will be impinged by droplets exceeding some minimum size up until the maximum sized droplet contained in the cloud atmosphere. Line 212 identifies the relation corresponding to the predetermined minimum size of super-cooled water droplets that contribute to ice accretion vs. location along the chord of the convex shaped housing. Droplets smaller than the minimum size will follow the airflow vectors and will not impinge the convex-shaped housing except at locations near the stagnation point. Dashed line 214 identifies the maximum size of super-cooled water droplets contained in the cloud atmosphere.

For a given size of a super-cooled water droplet (e.g., draw a horizontal line from any y-axis location), the exterior surface of the convex-shaped housing will be impinged for the stagnation point up to a maximum impingement location corresponding to the given size of super-cooled water droplet. Point 208 of relation 206 corresponds to the boundary location separating an ice accretion portion and an ice-free portion of the convex exterior surface for the cloud atmosphere having the maximum size of super-cooled water droplet corresponding to dashed line 214. Not all sizes of particles, however, contribute to ice accretion at every location within the ice accretion portion of the convex exterior surface. At point 208, relation 206 indicates that only super-cooled water droplets equal to the maximum size (or greater if the cloud atmosphere had greater sized particles) accrete at the boundary location. The region to the right of point 208 on graph 200 corresponds to the ice-free portion of the convex exterior surface, and points to the left of point 208 correspond to the ice-accretion portion of the convex exterior surface.

Vertical line 210 of relation 206 corresponds to the stagnation point of the convex exterior surface. At the stagnation point corresponding to vertical line 210, super-cooled water droplets of all sizes within the atmosphere contribute to ice accretion. Between point 208 and vertical line 210, super-cooled water droplets that have a size greater than a predetermined minimum will contribute to ice accretion. Super-cooled water droplets smaller than the predetermined minimum size will follow the flow vector lines and not impinge the convex exterior surface, and therefore will not contribute to ice accretion. Line 212 identifies the relation corresponding to the predetermined minimum size of super-cooled water droplets that contribute to ice accretion vs. location along the chord of the convex shaped housing.

The following are non-exclusive descriptions of possible embodiments of the present invention.

An exemplary embodiment relates to a system for measuring a maximum size of super-cooled water droplets in an airstream of an aircraft. The system includes a housing having a convex exterior surface on a forward end and having stabilizers projecting from an aft end. The system includes a gimballed mounting mechanism configured to attach the housing to an aircraft while permitting the housing to freely pitch and yaw with respect to the aircraft. In response to the airstream engaging the stabilizers, the housing aligns with a direction of the engaging airstream. Ice accretes on an ice-accretion portion of the convex exterior surface, in response to the housing engaging an airstream containing super-cooled water droplets. An aft-extent of the ice-accretion portion measured from the leading edge is indicative of the maximum size of the super-cooled water droplets.

The system of the preceding paragraph can optionally include, additionally and/or alternatively, any one or more of the following features, configurations and/or additional components:

A system for measuring a maximum size of super-cooled water droplets in an airstream of an aircraft according to an exemplary embodiment of this disclosure, among other possible things can further include a sequence of indices on the convex exterior surface extending from a leading index at a leading edge of the convex exterior housing through a sequence of increasingly-aft indices. Each of the sequence of indices can be visible in the absence of ice accretion. The indices in an ice-free portion of the sequence can indicate the maximum size of the super-cooled water droplets.

Any of the foregoing systems can further include an ice detector configured to detect ice accretion on at least a specific one of the sequence of ice-accretion portion. Any of the foregoing systems can further include an alert system configured to generate, in response to detection by the ice detector of ice accretion on the specific one of the sequence of ice-accretion portion, an alert.

Any of the foregoing systems can further include a boundary locator configured to determine the aft-extent of the ice-accretion portion.

Any of the foregoing systems can further include a signal generator configured to generate a signal indicative of the determined aft-extent of the ice-accretion portion.

Any of the foregoing systems can further include a cooling system configured to actively cool the convex exterior surface of the housing.

Any of the foregoing systems can further include a droplet-size calculator configured to calculate a sequence of water-droplet sizes, each corresponding sequence of aft-extents, wherein each of the calculated water-droplet sizes correspond to a droplet size, below which water droplets do not cause ice-accretion portion having the corresponding aft-extent.

Any of the foregoing systems can further include a camera configured to obtain images of the convex exterior surface.

Any of the foregoing systems can further include a heater configured to heat the convex exterior surface so as to melt, evaporate and/or sublimate any ice accreted thereto.

Any of the foregoing systems can further include a temperature control system configured to provide cycles of operation that include a heating portion and an accretion portion of each of the provided cycles, wherein the heater is activated during the heating portion, and the heater is deactivated during the accretion portion.

A further embodiment of any of the foregoing fan drive gear system, wherein the gimballed mounting mechanism includes a ball and socket mechanism, A further embodiment of any of the foregoing fan drive gear systems, wherein the gimballed mounting mechanism includes a yaw rotation mechanism and a pitch rotation mechanism.

Some embodiments relate to a method for providing visual indication of a maximum size of super-cooled water droplets in an airstream of an aircraft. The method includes engaging the airstream by a housing having a convex exterior surface on a forward end and having stabilizers projecting from an aft surface. The method includes aligning, using the stabilizers, the housing in a direction of the engaged airstream. The method includes providing a sequence of visual indices corresponding to a sequence of ice-accretion regions, each of the sequence of indices visible in the absence of ice accretion. The method also includes accreting ice on one or more of the sequence of ice-accretion regions when the engaged airstream contains super-cooled water droplets.

The method of the preceding paragraph can optionally include, additionally and/or alternatively, any one or more of the following features, configurations and/or additional components:

A method for measuring a maximum size of super-cooled water droplets in an airstream of an aircraft according to an exemplary embodiment of this disclosure, among other possible things can further include identifying a test location corresponding to one of the ice-accretion regions, the test location corresponding to a calculated boundary that separates an ice-accretion portion and an ice-free portion of the convex exterior surface in atmospheric conditions having super-cooled water droplets no larger than a maximum size.

Any of the foregoing methods can further include monitoring the identified test location to detect whether ice has accreted thereon.

Any of the foregoing methods can further include generating an alert signal in response to detecting ice accretion on the monitored test location.

A further embodiment of any of the foregoing methods, wherein identifying the test location includes calculating, based on at least one of: airspeed and total air temperature, a boundary location on the convex exterior surface, the boundary location corresponding to a predicted aft-extent of ice-accretion corresponding to a predetermined maximum size of super-cooled water droplets.

A further embodiment of any of the foregoing methods, wherein monitoring the determined test location includes imaging the convex exterior surface using a camera.

A further embodiment of any of the foregoing methods, wherein monitoring the determined test location further includes processing a test pixel of an image obtained by the camera, the test pixel imaging the determined test location.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A system for indicating a maximum size of super-cooled water droplets in an airstream of an aircraft, the system comprising:
a housing having a convex exterior surface on a forward end and having stabilizers projecting from an aft end;
a sequence of indices on the convex exterior surface extending from a leading index at a leading edge of the convex exterior housing through a sequence of increasingly-aft indices, each of the sequence of indices being visible in the absence of ice accretion; and
a gimballed mounting mechanism configured to attach the housing to an aircraft while permitting the housing to freely pitch and yaw with respect to the aircraft, wherein, in response to the airstream engaging the stabilizers, the housing aligns with a direction of the engaging airstream;
wherein ice accretes on an ice-accretion portion of the convex exterior surface, in response to the housing engaging an airstream containing super-cooled water droplets,
wherein an aft-extent of the ice-accretion portion measured from the leading edge is indicative of the maximum size of the super-cooled water droplets, the indices on an ice-free portion of the convex exterior surface indicating the maximum size of the super-cooled water droplets.

2. The system of claim 1, further comprising:
an ice detector configured to detect ice accretion on at least a specific one of the sequence of ice-accretion portion.

3. The system of claim 2, further comprising:
an alert system configured to generate, in response to detection by the ice detector of ice accretion on the specific one of the sequence of ice-accretion portion, an alert.

4. The system of claim 1, further comprising:
a boundary locator configured to determine the aft-extent of the ice-accretion portion.

5. The system of claim 4, further comprising:
a signal generator configured to generate a signal indicative of the determined aft-extent of the ice-accretion portion.

6. The system of claim 1, further comprising:
a cooling system configured to actively cool the convex exterior surface of the housing.

7. The system of claim 1, further comprising:
a droplet-size calculator configured to calculate a sequence of water-droplet sizes, each corresponding sequence of aft-extents, wherein each of the calculated water-droplet sizes correspond to a droplet size, below which water droplets do not cause ice-accretion portion having the corresponding aft-extent.

8. The system of claim 1, further comprising:
a camera configured to obtain images of the convex exterior surface.

9. The system of claim 1, further comprising:
a heater configured to heat the convex exterior surface so as to melt, evaporate and/or sublimate any ice accreted thereto.

10. The system of claim 9, further comprising:
a temperature control system configured to provide cycles of operation that include a heating portion and an accretion portion of each of the provided cycles, wherein the heater is activated during the heating portion, and the heater is deactivated during the accretion portion.

11. The system of claim 1, wherein the gimballed mounting mechanism includes a ball and socket mechanism.

12. The system of claim 1, wherein the gimballed mounting mechanism includes a yaw rotation mechanism and a pitch rotation mechanism.

13. A method for indicating a maximum size of super-cooled water droplets in an airstream of an aircraft, the method comprising:
attaching, via a gimballed mounting mechanism, a housing to the aircraft, the housing having a convex exterior surface on a forward end and having stabilizers projecting from an aft end;
permitting, via the gimballed mounting mechanism, the housing to freely pitch and yaw with respect to the aircraft;
engaging the airstream by the housing;
aligning, using the stabilizers and in response to the engaged airstream, the housing in a direction of the engaged airstream;
providing a sequence of visual indices on the convex exterior surface of the housing, the sequence of visual indices corresponding to a sequence of ice-accretion regions, each of the sequence of indices being visible in the absence of ice accretion; and
accreting ice on one or more of the sequence of ice-accretion regions when the engaged airstream contains super-cooled water droplets,
wherein an aft-extent of the ice-accretion portion measured from the leading edge is indicative of the maximum size of the super-cooled water droplets, the indices in an ice-free portion of the sequence indicating the maximum size of the super-cooled water droplets.

14. The method of claim 13, further comprising:
identifying a test location corresponding to one of the ice-accretion regions, the test location corresponding to a calculated boundary that separates an ice-accretion portion and an ice-free portion of the convex exterior surface in atmospheric conditions having super-cooled water droplets no larger than a maximum size.

15. The method of claim 14, further comprising:
monitoring the identified test location to detect whether ice has accreted thereon.

16. The method of claim 15, further comprising:
generating an alert signal in response to detecting ice accretion on the monitored test location.

17. The method of claim 15, wherein monitoring the identified test location comprises:
imaging the convex exterior surface using a camera.

18. The method of claim 15, wherein monitoring the identified test location further comprises:
processing a test pixel of an image obtained by the camera, the test pixel imaging the identified test location.

19. The method of claim 14, wherein identifying the test location comprises:
calculating, based on at least one of: airspeed and total air temperature, a boundary location on the convex exterior surface, the boundary location corresponding to a predicted aft-extent of ice-accretion corresponding to a predetermined maximum size of super-cooled water droplets.

* * * * *